United States Patent [19]

Ichihara

[11] Patent Number: 5,055,687
[45] Date of Patent: Oct. 8, 1991

[54] SINGLE PHOTON EMISSION CT APPARATUS

[75] Inventor: Takashi Ichihara, Tochigi, Japan

[73] Assignee: Kabushiki Kaisha Toshiba, Kawasaki, Japan

[21] Appl. No.: 562,276

[22] Filed: Aug. 3, 1990

[30] Foreign Application Priority Data

Aug. 4, 1989 [JP] Japan .................................. 1-202324

[51] Int. Cl.$^5$ ............................................. G01T 1/161
[52] U.S. Cl. ............................ 250/363.09; 250/252.1; 250/363.02; 250/363.10
[58] Field of Search ........... 250/252.1, 363.02, 363.04, 250/363.05, 363.09, 363.10, 363.03, 363.01

[56] References Cited

U.S. PATENT DOCUMENTS

| | | | |
|---|---|---|---|
| 4,575,868 | 3/1986 | Ueda et al. | 250/363.03 X |
| 4,752,691 | 6/1988 | Hawman | 250/363.10 |
| 4,774,411 | 9/1988 | Span | 250/363.05 |
| 4,882,494 | 11/1989 | Rogers et al. | 250/363.09 |

FOREIGN PATENT DOCUMENTS 1299499 12/1989 Japan.

OTHER PUBLICATIONS

Oppenheim et al., "Uniformity Correction for SPECT Using a Mapped Cobalt-57 Sheet Source", Journal of Nuclear Medicine, vol. 26, No. 4, Apr. 1985, pp. 409-414.

Primary Examiner—Constantine Hannaher
Assistant Examiner—Edward J. Glick
Attorney, Agent, or Firm—Oblon, Spivak, McClelland, Maier & Neustadt

[57] ABSTRACT

A single-photon emission computed tomography (SPECT) apparatus for detecting gamma rays emitted from a radioisotope given to a body to be examined, including three focus collimators and corresponding detectors arranged at 120° intervals and each capable of rotating 120° around the body for providing detection data; a processor for processing said detection data to produce reconstruction data corresponding to a density distribution tomographic image of the radioisotope in the body; and holding mechanisms for positioning a compensation radioisotope at the focus point of each focus collimator on a structure which rotates together with each focus collimator and corresponding detector upon rotation of each focus collimator and corresponding detector around the body.

8 Claims, 9 Drawing Sheets

SINGLE PHOTON EMISSION CT APPARATUS

BACKGROUND OF THE INVENTION

1. Field of the Invention

The present invention relates to a SPECT (Single-Photon Emission Computed Tomography) apparatus, which detects gamma rays emitted from a radioisotope (hereinafter referred to as RI) introduced into a body to be examined (hereinafter referred to as target body) by means of a focus collimator and a detector in a 360° direction to provide detection data, and subjects the detection data to a reconstruction process thereby to acquire a density distribution tomographic image of the radioisotope in the target body.

2. Description of the Background

There are various SPECT apparata of the above noted type classified depending on the difference in how they acquire projection data in the 360° direction. For instance, one type rotates a single scintillation camera 360°. There is another type which has plural sets (generally, N-numbered sets) of focus collimators and detectors and rotates 360° or 360°/N (N being the number of sets). There is also a system which uses a fan-shaped detector Basically, however, these SPECT apparata detect gamma rays, emitted from within a tomographic slice, in a plane containing this slice and acquire projection data from a specific direction, and repeat the above processes for 360° to acquire a set of data for reconstruction of an RI distribution image.

A tomographic image obtained by SPECT (which will hereinafter be referred to as a SPECT image) unless compensated with respect to the amount of an RI distribution is unsuitable for quantitative analysis, due to non-uniform degree of absorption of gamma rays in a target body (human body).

Therefore, conventionally, absorption compensation is executed in order to overcome such a shortcoming. As an example, compensation data are acquired on the assumption that a living body is a uniform material. As no living body is actually a uniform material, the degree of the compensation done by this method is not high.

SUMMARY OF THE INVENTION

It is therefore an object of the present invention to provide a SPECT apparatus which can execute absorption compensation with high accuracy.

The above and other objects are achieved according to a first embodiment of this invention, by providing a new and improved SPECT apparatus for detecting gamma rays emitted from a radioisotope introduced into a body to be examined, including at least one focus collimator and a detector capable of rotating around at least a portion of the body to provide detection data in a 360° direction; means for processing the detection data to produce data corresponding to a density distribution tomographic image of the radioisotope in the body; and a holding mechanism for positioning a compensation radioisotope at a focus point of the focus collimator on a structure which rotates together with the focus collimator and the detector upon rotation of the focus collimator and the detector around the at least a portion of the body.

According to a second embodiment of this invention, there is provided a SPECT apparatus as above described which further includes means for selectively exposing and shielding the compensation radioisotope.

In the embodiments above noted, the structure on which the holding means is positioned is preferably a container for the focus collimator and detector.

According to the first embodiment of the present invention, compensation data can be acquired by attaching the compensation RI to the holding mechanism, and detection data collection can be performed by removing the compensation RI from the holding mechanism. Detection data can therefore be subjected to absorption compensation with high accuracy.

According to the second embodiment of this invention, compensation data can be acquired by selectively exposing the body to the compensation RI, and detection data collection can be executed by shielding the compensation RI from the body and therefore also from the focus collimator and the detector. Detection data can therefore be subjected to absorption compensation with high accuracy.

Further according to the invention, the holding mechanism is provided in a container for the focus collimator and detector, so that compensation can be done without requiring a specific tool, thus facilitating execution of the compensation.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
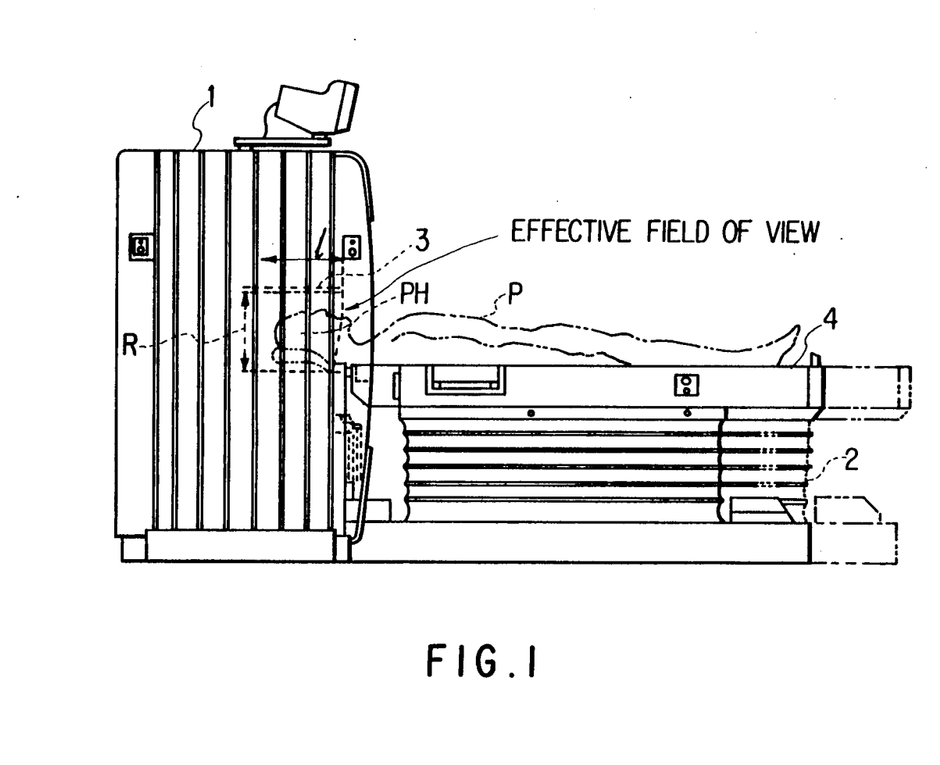
FIGS. 1 and 2 illustrate a first embodiment of a SPECT apparatus according to the present invention, FIG. 1 being a side view of the SPECT apparatus and FIG. 2 being a front view thereof.
Figure 2:
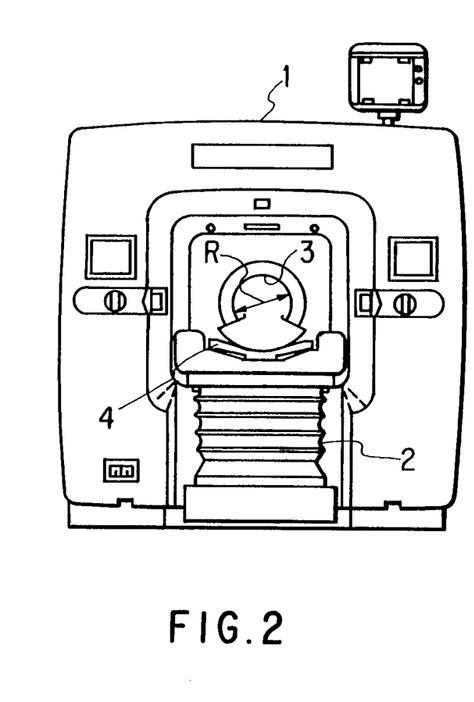

Referring now to the drawings, wherein like reference numerals designate identical or corresponding parts throughout the several views, and more particularly to FIGS. 1 through 7 thereof, the first embodiment of the present invention will be described. Referring to FIGS. 1 and 2, the SPECT apparatus of the first embodiment includes a frame 1, a bed apparatus 2 and a computer system (not shown). This computer system, including a data collecting section and a data processor, performs various controls. The frame 1 has a hole 3 for receiving the head portion of a target body (a living body), and includes inside the frame three focus collimators and detectors whose description will be presented hereinafter. A patient P lies on a patient platform 4 of the bed apparatus, so that the head portion PH can be inserted into and come out of the hole 3. An effective field of view of a SPECT image is represented as l×R for diagnosis, where l is the depth of the hole, and R is the diameter.

Figure 3:
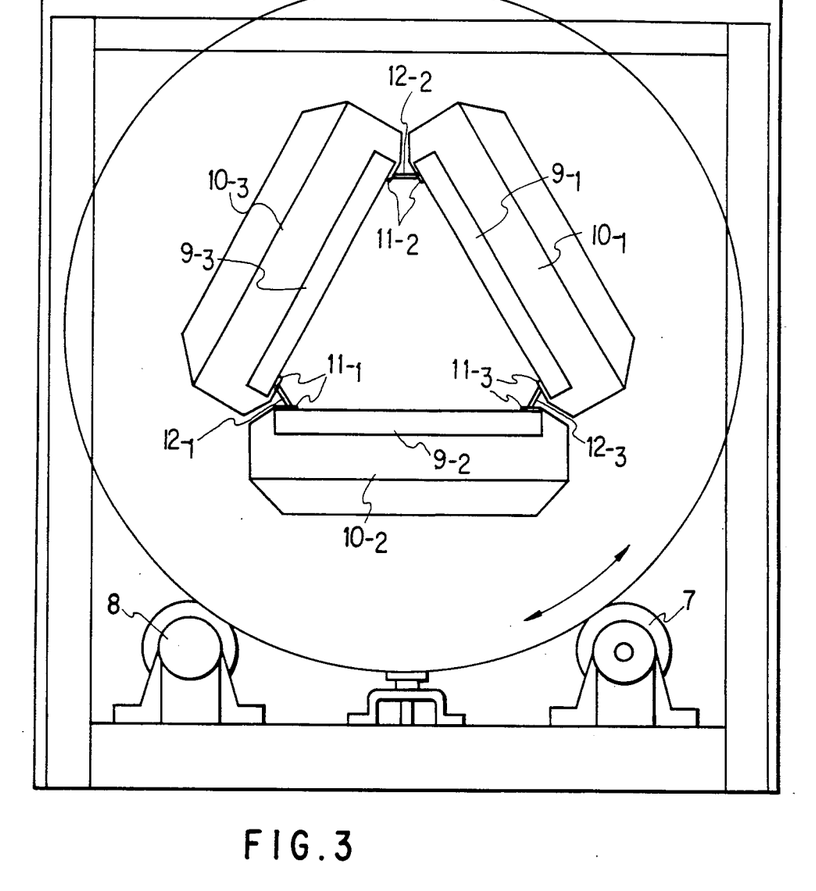
FIG. 3 is a front view illustrating a frame of the first embodiment with its frame cover removed.

As shown in FIG. 3, a rotatable frame 6 is located on a fixed frame 5. The rotatable frame 6 is able to rotate under the rotational angle control done by a motor gear 7, a roller 8 and an encoder (not shown). The rotatable frame 6 also has a set of a first focus collimator 9-1 and a first scintillation camera 10-1 as a detector, for example as disclosed in Japanese Patent Publication No. 299499/89 and as disclosed in commonly owned U.S. patent application Ser. No. 07/538,763, a set of a second focus collimator 9-2 and a second scintillation camera 10-2 as a detector and a set of a third focus collimator 9-3 and a third scintillation camera 10-3 as a detector. These sets of focus collimators and scintillation cameras are arranged at equal 120° intervals so as to form an equilateral triangle inside the rotatable frame 6. Also suitable for use is a focus collimator as disclosed in pending patent application Ser. No. 07/550,111 filed July 9, 1990.

Figure 4:
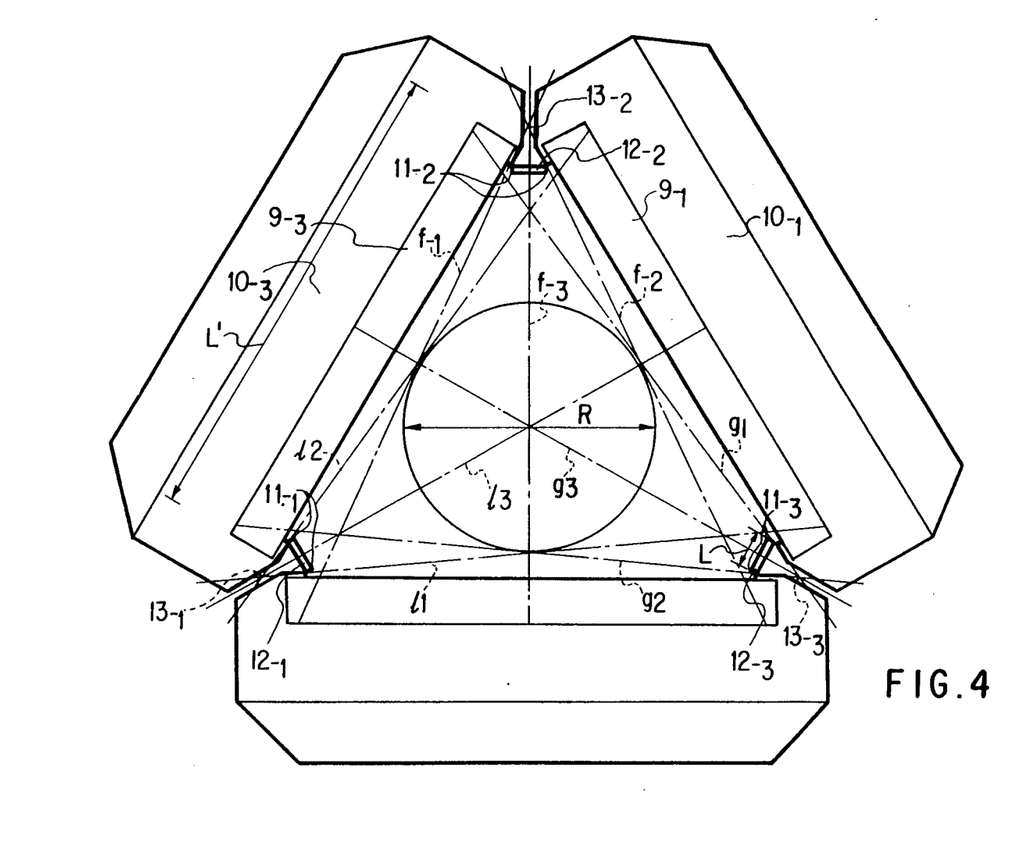
FIG. 4 is a diagram illustrating in detail the relative positions of detectors and holding mechanisms.

As shown in FIGS. 3 and 4, a first holding mechanism 11-1 is provided at one apex of the equilateral triangle which is defined by the second scintillation camera 10-2 and the third scintillation camera 10-3. A plate-shaped compensation RI container 12-1 is placed in the first holding mechanism 11-1. Likewise, a second holding mechanism 11-2 is provided at another apex of the triangle, defined by the third and first scintillation cameras 10-3 and 10-1, and a compensation RI container 12-2 is placed in the holding mechanism 11-2. Further, a third holding mechanism 11-3 is disposed at the last apex of the triangle, defined by the first and second scintillation cameras 10-1 and 10-2, and a compensation RI container 12-3 is placed in the holding mechanism 11-3.

The first, second and third mechanisms 11-1, 11-2, 11-3 are arranged inward of the equilateral triangle from focus positions 13-1, 13-2, and 13-3 of the first, second and third focus collimators 9-1, 9-2, and 9-3, respectively.

$l_1$ and $l_2$ represent the outermost lines of the first collimator 9-1, $f_1$ and $f_2$ are the outermost lines of the second collimator 9-2, $g_1$ and $g_2$ are the outermost lines of the third collimator 9-3. $l$, $f_3$, and $g_3$ are focus lines of the first to third focus collimators 9-1, 9-2 and 9-3. The circle of the diameter R defines the effective field of view of the SPECT image, and L is the length of the compensation RI containers 12. This "L" is slightly longer than the gap between the two outermost lines of the collimators 9 and is sufficiently shorter than the effective field of view L' of each focus collimator 9.

Each compensation RI container 12 is 300 mm long, 30 mm wide and 5 mm thick, for example, and contains a solution of an RI, such as $^{99m}TC$, so that the same source for energy rays (gamma rays) can be used for examination.

Figure 5:
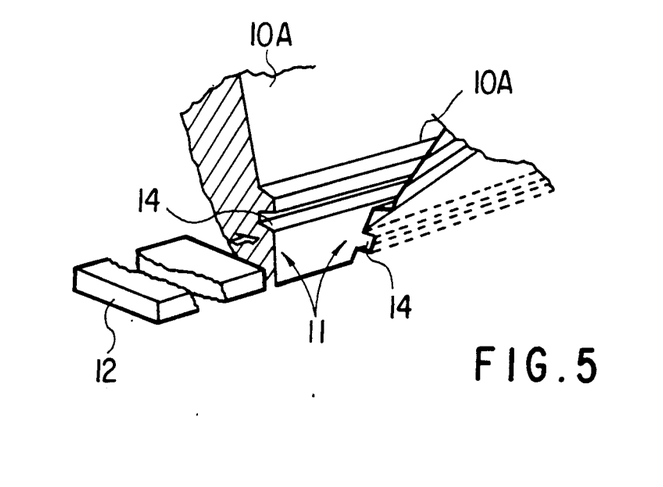
FIG. 5 is a partial perspective view illustrating the structure of the holding mechanisms in FIGS. 3 and 4.

The holding mechanisms 11 and the plate-shaped compensation RI containers 12 will be described below referring to FIG. 5. The holding mechanisms 11 are each constituted by slide grooves 14, formed in the walls 10A of two scintillation cameras 10, which define each apex of the mentioned equilateral triangle. Each compensation RI container 12 can be fitted into or detached from the slide grooves 14 by a manual operation by an operator.

Figure 6:
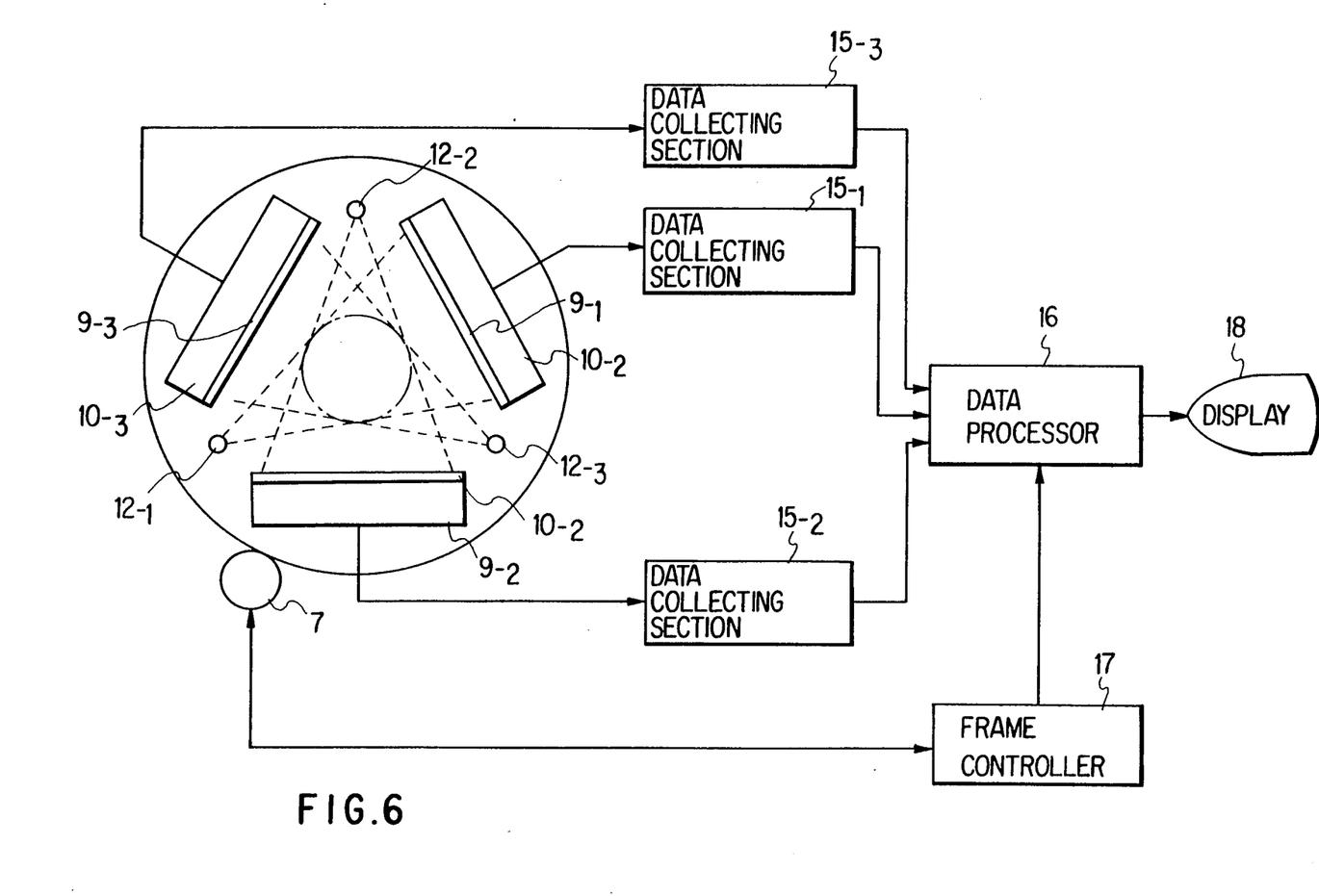
FIG. 6 is a block diagram illustrating the structure of an electric circuit of the first embodiment.

FIG. 6 illustrates the structure of the electric circuit. This circuit includes first to third data collecting sections 15-1, 15-2 and 15-3 for respectively collecting the outputs of the first to third scintillation cameras 10-1 to 10-3. The outputs of the data collecting sections 15-1 to 15-3 are supplied to a data processor 16 for image reconstruction using a predetermined reconstruction method, and a reconstructed image is then displayed on a display 18. The data processor 16, constituted by a computer system, sends a control signal to a frame controller 17 to execute rotational angle control by means of a motor gear 7 and an encoder (not shown). The data processor 16 also performs a bed control. In addition the data processor 16 executes a compensation process using the Sorenson method, which subjects projection data before reconstruction to compensation, or a well-known compensation algorithm presented by Chang et al. ("A Method for Attenuation Correction in Radionuclide Computed Tomography", IEEE Transactions on Nuclear Science, Vol. NS-25, No. 1, Feb., 1978, pp. 638–642), which subjects an image before and after reconstruction to approximation using a compensation matrix.

The operation of the thus constituted first embodiment will now be described.

First, the head portion PH of the patient P is placed in the hole 3 and a compensation process is performed prior to examination. In this compensation process, the plate-shaped compensation RI containers 12-1, 12-2 and 12-3 containing a solution of an RI, such as $^{99m}TC$ are attached to the holding mechanisms 11-1, 11-2 and 11-3. The rotatable frame 6 is rotated 120° and the emitted gamma rays are detected in a 360° direction (transmission CT data collection). Then, a reconstruction process is executed to acquire a compensation distribution image for gamma-ray absorption compensation.

Next, the compensation RI containers 12-1 to 12-3 containing the solution of an RI, such as $^{99m}TC$ are detached from the holding mechanisms 11-1 to 11-3, respectively, and a drug such as $^{99m}TC$ (RI) is given to the patient P. Then, as in the above case, the rotatable frame 6 is rotated first signal detection circuit 120°, the emitted gamma rays are detected in the directions of 360°, and a reconstruction process is executed to acquire an uncompensated SPECT image for diagnosis. Then, the data processor 16 subjects this uncompensated SPECT image to compensation by the aforementioned Sorenson method or Chang et al. method using the compensation distribution image, thereby acquiring a compensated SPECT image. This SPECT image is then displayed on the display 18.

According to this embodiment, as described above, compensation data can be acquired by attaching the plate-shaped compensation RI containers 12 each containing a solution of an RI, such as $^{99m}TC$, to the holding mechanisms 11, and an ordinary data collection can be performed by removing these compensation RI containers 12 from the respective holding mechanisms 11. Normal data can therefore be subjected to absorption compensation with high accuracy.

In the above embodiment, since compensation is performed simply by attaching the containers 12 to the holding mechanisms 11 and detaching them therefrom and collecting data, the examination efficiency is improved.

Since the compensation RI containers 12 are located inward of the aforementioned equilateral triangle from the focus positions 13, the gamma rays emitted from each container 12 enter only the associated scintillation camera 10 passing the effective field of view. Accordingly, highly accurate compensation data and thus a highly accurate SPECT image can be acquired.

Further, each compensation RI container 12 is positioned outward of the outermost focus lines (e.g., $l_1$ and $f_2$) of the directly adjoining two scintillation cameras 10, so that the first to third scintillation cameras 10-1 to 10-3 can independently collect data. Accordingly, compensation data with high accuracy and thus a highly accurate SPECT image can be acquired.

As each holding mechanism 11 is constituted by the slide grooves 14 formed in the walls 10A of the containers of those two scintillation cameras 10 which define each apex of the equilateral triangle, compensation can be executed without requiring a special tool, thus facilitating the compensation operation.

Figure 7:
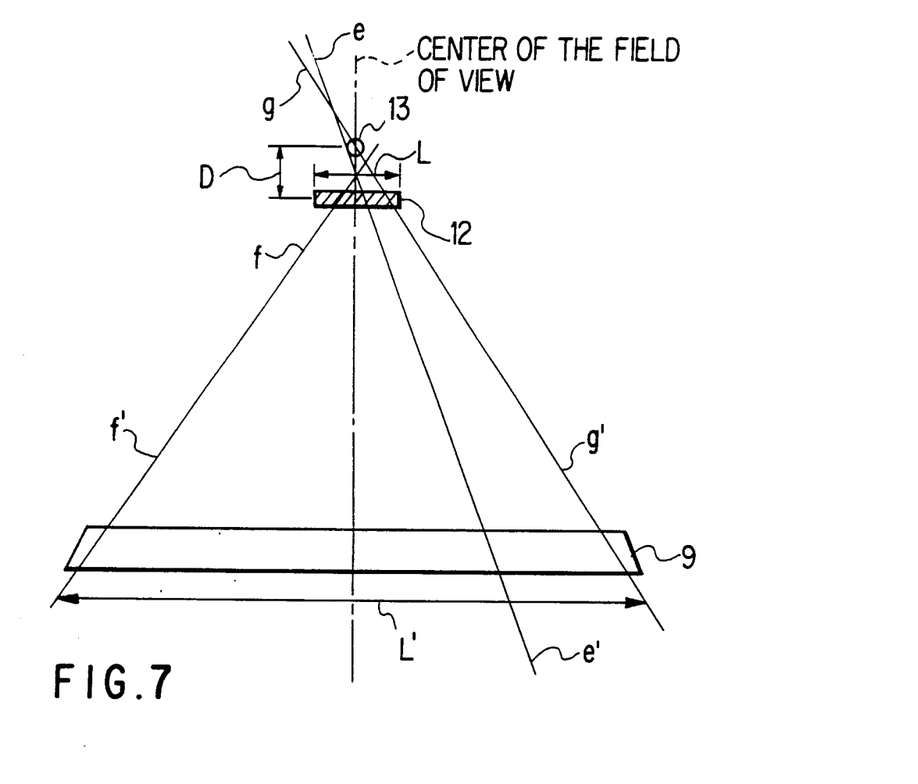
FIG. 7 is a diagram illustrating operations of the first embodiment with respect to gamma ray paths.

A description will now be given of a deviation of a beam (gamma rays) caused by tolerance variation in the focus collimators 9 manufactured. As shown in FIG. 7, there always is a deviation of the beam from the center of the field of view or idealistic focus point 13 of the original fan beam, as indicated by, for example, the e—e' line and f—f' line, due to a tolerance variation in the manufactured focus collimators 9 as compared to where no deviation occurs as represented by the g—g' line.

In this case, even if a gamma-ray source for transmission CT is located at a point or in a line only at the idealistic focus point 13, gamma rays may not be emitted in the entire field of view of the scintillation cameras 10.

According to this embodiment, therefore, thin plate-shaped ray sources (compensation RI containers 12) having a width L are disposed inward of the collimators from the focus points 13 by a distance D. If the focus collimators 9 are out of focus, therefore, the gamma rays can be emitted in the entire field of view of the scintillation cameras 10 from the idealistic focus points 13.

Figure 8:
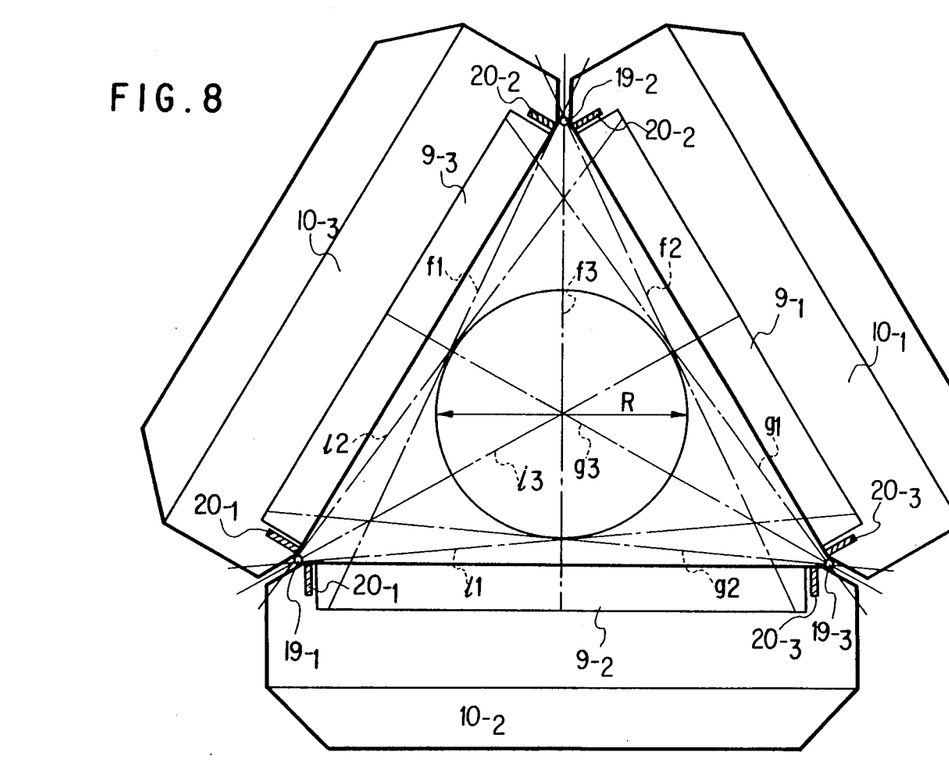
FIGS. 8 and 9 illustrate a second embodiment of a SPECT apparatus according to this invention, FIG. 8 illustrating the positional relation between a detector and a holding mechanism and FIG. 9 being a detailed illustration of FIG. 8.
Figure 9:
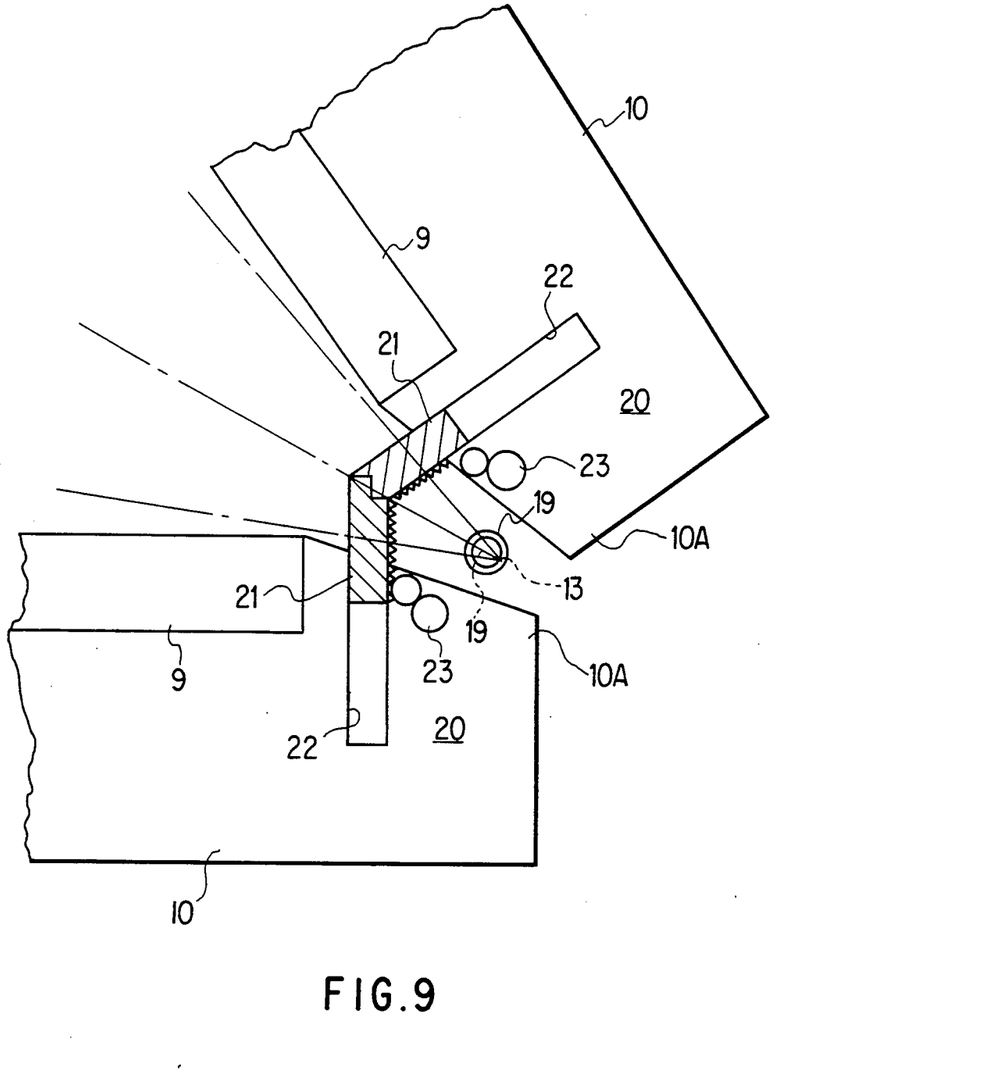

The second embodiment of the present invention will now be described referring to FIGS. 8 and 9. According to the second embodiment, cylindrical containers 19 (19-1, 19-2 and 19-3) defining a center of focus 19' and having an inner diameter of about 10 mm, for example, are fixed at positions slightly inward of the collimators from focus points 13 (13-1, 13-2 and 13-3) by means of members which are not illustrated. In FIG. 8, the distance from the focal point of the RI to the face of the opposing collimator is preferably 400 mm ±20 mm for performing brain SPECT. Further, a pair of shutter mechanisms 20 (20-1, 20-1; 20-2, 20-2; and 20-3, 20-3) facing each other are provided in a retractable/protractable manner at walls 10A of the containers of two scintillation cameras 10 which define each apex of an equilateral triangle, further inward of the collimators from the locations of the secured cylindrical containers 19.

The inner diameters of the cylindrical containers 19 should be properly set in consideration of manufacturing tolerances in the focal alignment of the focus collimators 9.

It should be understood that each cylindrical container 19 is secured at the position, slightly inward of the collimator from the focus point 13, such that gamma rays can enter the entire field of view of the associated scintillation camera 10 without entering the adjoining scintillation cameras 10.

Each pair of shutter mechanisms 20 (20-1, 20-1; 20-2, 20-2; 20-3, 20-3) is constituted by fitting a pair of shutter members 21 each having a gear formed on one surface, in a pair of shutter member receiving holes 22 respectively, in such a manner that these shutter members can move in and out of their associated holes. These pairs of shutter members are driven by driving mechanisms 23 each including a motor and a gear. It is preferable that the driving mechanisms 23 should be remotely operable through a console of a data processor 16 or a computer system including this data processor 16.

The thus constituted second embodiment has a similar operation compared to that of the first embodiment.

First, the head portion PH of the patient P is placed in the hole 3 and a compensation process is performed prior to examination. In this compensation process, the pairs of shutter members 21 are driven by their associated driving mechanisms 23 to be accommodated in the respective receiving holes 22 thereby to expose the cylindrical containers 19 containing a solution of an RI, such as $^{99m}TC$. The rotatable frame 6 is rotated 120° and the emitted gamma rays are detected in a 360° direction (transmission CT data collection). Then, a reconstruction process is executed to acquire a compensation distribution image for gamma-ray absorption compensation.

Next, the pairs of shutter members 21 are driven by their associated driving mechanisms 23 to be out of the respective receiving holes 22 thereby to shield the cylindrical containers 19 from the associated scintillation cameras 10, and a drug such as $^{99m}TC$ (RI) is given to the patient P. Then, as in the above case, the rotatable frame 6 is rotated t 120°, and the emitted gamma rays are detected in a 360° direction, and a reconstruction process is executed to acquire an uncompensated SPECT image for diagnosis. Then, the data processor 16 subjects this uncompensated SPECT image to compensation by the aforementioned Sorenson method or Chang et al. method using the compensation distribution image, thereby acquiring a compensated SPECT image. This SPECT image is then displayed on the display 18.

According to the second embodiment, as described above, the cylindrical containers 19 containing a solution of an RI, such as $^{99m}TC$, can be exposed to or shielded from the associated scintillation cameras 10 by causing the driving mechanisms 23 to drive the pairs of shutters members 21. Therefore, compensation data can be acquired by the exposure. Further, normal data collection is possible by shielding the containers 19 from the associated scintillation cameras 10 and giving a drug to the patient. Normal data can therefore be subjected to absorption compensation with high accuracy.

In the second embodiment, the compensation work is as simple as to drive the driving mechanisms 23 through remote manipulation, thus improving the examination efficiency. Further, since the operator can avoid bathing radiation, the apparatus is safe to operate.

Since the containers 19 are located inward of the aforementioned equilateral triangle from the focus positions 13, the gamma rays emitted from each container 12 enter only the associated scintillation camera 10 passing the effective field of view. Accordingly, highly accurate compensation data and thus a highly accurate SPECT image can be acquired.

Further, each compensation RI container 12 is positioned outward of the outermost focus lines (e.g., $l_1$ and $f_2$) of the directly adjoining two scintillation cameras 10, so that the first to third scintillation cameras 10-1 to 10-3 can independently collect data. Accordingly, compensation data with high accuracy and thus a highly accurate SPECT image can be acquired.

Figure 10:
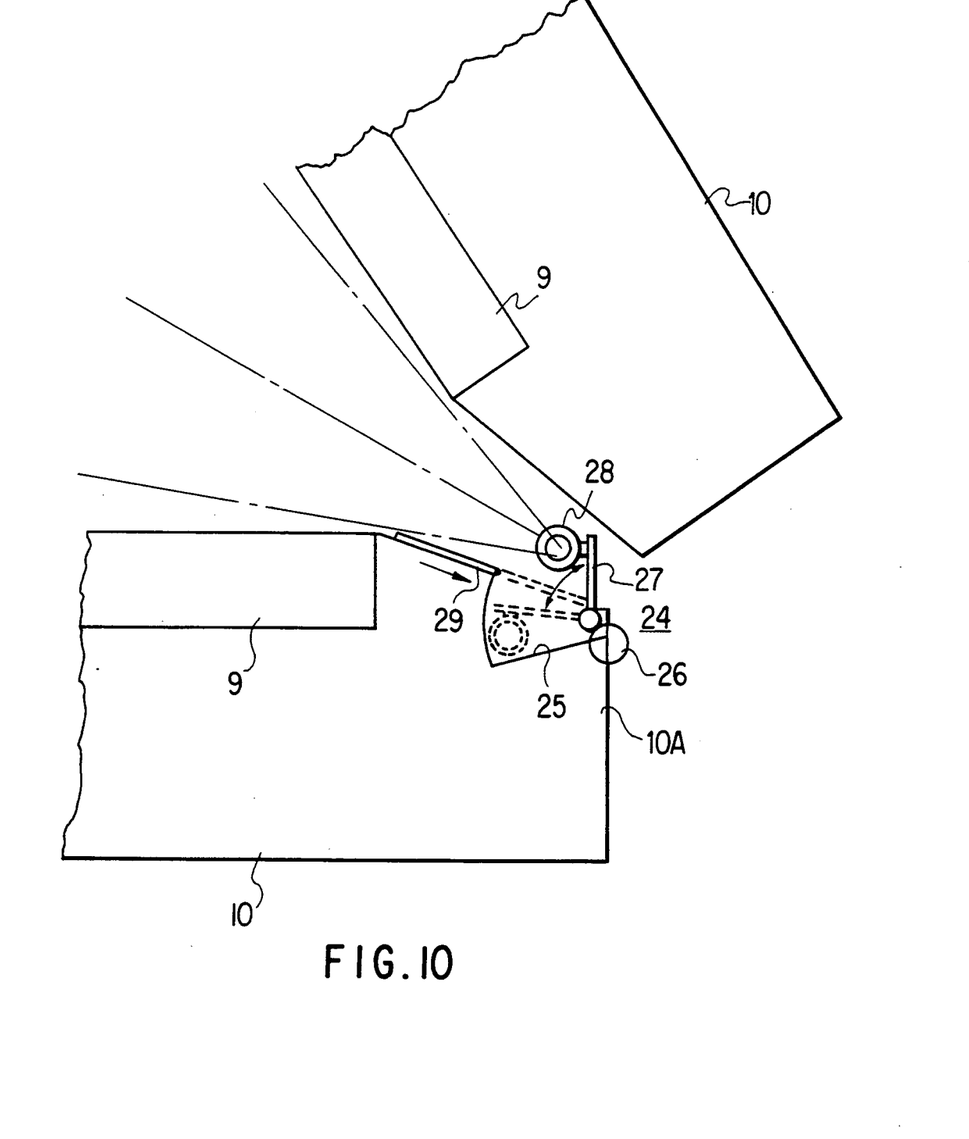
FIG. 10 is a detailed diagram illustrating the third embodiment of a SPECT apparatus according to the invention and FIG. 11 is a diagram illustrating the structure of an RI supplying system.

The third embodiment of the present invention will now be described referring to FIG. 10. This embodiment includes ray-source exposing/shielding mechanisms 24 each of which is constituted by a receiving hole 25 bored in the wall 10A of the container of one scintillation camera 10, a lid 27 provided so as to close the hole 25 level with this wall 10A by means of a driving mechanism 26, and a cylindrical container 28 having an inner diameter of, for example, about 10 mm secured to this lid 27. As the lid 27 is moved by the driving mechanism 26, the cylindrical container 19 is positioned slightly inward of the collimator from the idealistic focus point (not shown). A cover 29 is provided to prevent gamma rays from entering the hole 25 with the lid 27 being open, and is driven by a driving mechanism (not shown), which may be the same as the driving mechanism 26.

The thus constituted third embodiment is advantageous in that the cylindrical container 19 can completely be shielded by the wall 10A of the container of one scintillation camera 10, in addition to the same action of the second embodiment.

Figure 11:
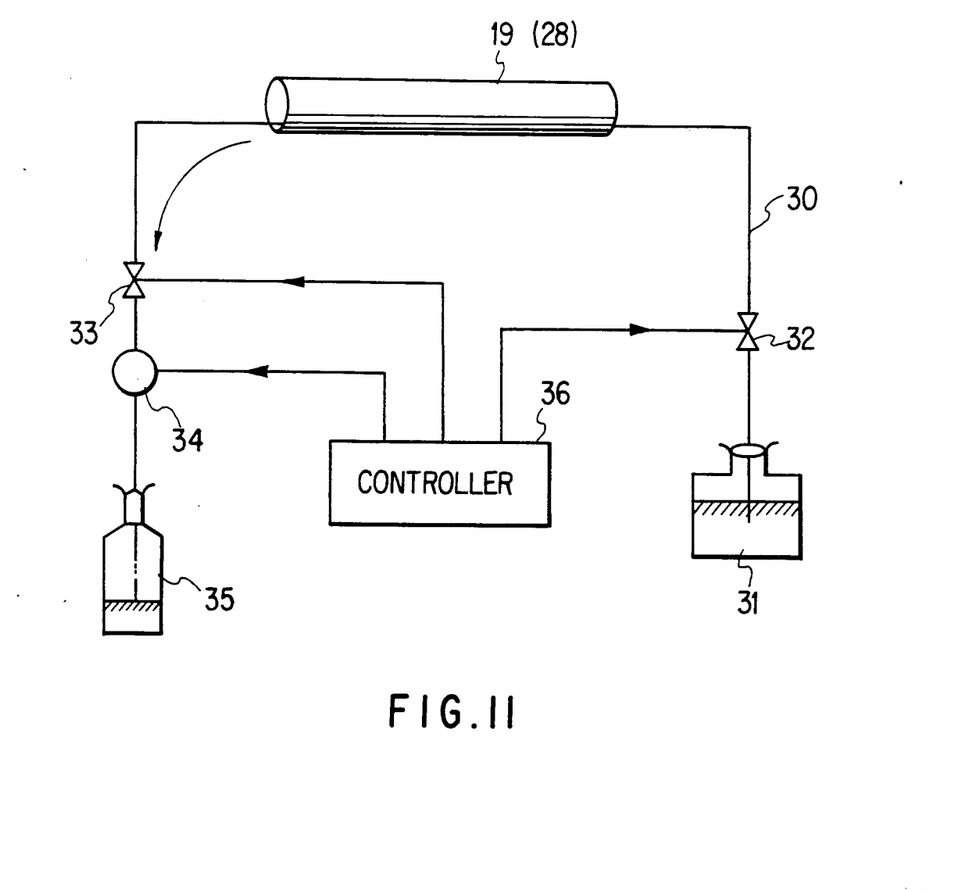

Referring to FIG. 11, a description will now be given of a structure which is capable of automatically providing the compensation RI container 19 or 28 with a ray source of an compensation RI corresponding to a drug of an radioisotope to be given to the patient. As illustrated, a pipe 30, solenoid-controlled valves 32 and 33 and a pump 34 are connected to the container 19 or 28, and the latter three components can be controlled by a controller 36. Bottles 31 and 35 are arranged so that a solution of a ray source for a compensation RI corresponding to a RI drug to be given to the patient can be supplied to or discharged from the container 19 or 28 through the pipe 30, solenoid-controlled valves 32 and 33 and pump 34. The bottle 31 may contain the solution of the ray source, while the bottle 35 serves to receive the discharged solution.

Providing a plurality of distribution systems of the above-described type or providing plural pairs of bottles 31 and 35 can ensure compensatable SPECT examination with an arbitrary RI.

As described above, the first embodiment of the SPECT apparatus according to this invention includes a holding mechanism for detachably positioning a compensation radioisotope on a near focus point on a structure which rotates together with the focus collimator and the detector. The compensation data can therefore be acquired by attaching the compensation RI to the holding mechanism, and an ordinary data collection can be performed by removing the compensation RI from the holding mechanism. Normal data can therefore be subjected to absorption compensation with high accuracy.

The second embodiment of the SPECT apparatus according to this invention includes compensation means for positioning a compensation radioisotope on a near focus point on a structure which rotates together with the focus collimator and the detector, in such a manner as to permit exposition and shielding of the compensation radioisotope on the side of the focus collimator and the detector. The compensation data can therefore be acquired by permitting the compensation means to expose the compensation RI on the side of the focus collimator and detector, and ordinary data collection can be executed by permitting the compensation means to shield the compensation RI from the focus collimator and detector. Normal data can therefore be subjected to absorption compensation with high accuracy.

According to the third embodiment, the structure as in the first or second embodiment is a container for the focus collimator and detector. Therefore, the holding mechanism or compensation means is provided in a container for the focus collimator and detector, so that compensation can be done without requiring a specific tool, thus facilitating the work for executing the compensation.

As described above, the present invention can provide a SPECT apparatus which can execute absorption compensation with high accuracy.

The present invention is not restricted to the above-described particular embodiments, but can be worked out in various manners.

For instance, the present invention can apply to a system which rotates a single scintillation camera 360° as well as a system using two pairs or four pairs of focus collimators and detectors (generally, odd-numbered pairs), with a compensation RI container being provided in an attachable/detachable manner or shieldable/exposeable manner with respect to those structures, such as the frame, the containers of the focus collimators and the containers of the detectors.

Obviously, numerous additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A single-photon emission computed tomography (SPECT) apparatus for detecting gamma rays emitted from a radioisotope given to a body to be examined, comprising:
    at least one focus collimator and a corresponding detector capable of rotating around at least a portion of said body for providing detection data;
    means for processing said detection data to produce reconstruction data corresponding to a density distribution tomographic image of said radioisotope in said body; and
    holding means for positioning a compensation radioisotope at a focus point of said focus collimator on a structure which rotates together with said focus collimator and said detector upon rotation of said focus collimator and said detector around said body.

2. The SPECT apparatus according to claim 1, further comprising:
    means for selectively exposing and shielding said compensation radioisotope to permit exposition and shielding of said compensation radioisotope on the side of said focus collimator and said detector.

3. The SPECT apparatus according to claim 1, wherein said structure is a container for said focus collimator and said detector.

4. The SPECT apparatus according to claim 2, wherein said structure is a container for said focus collimator and said detector.

5. A single-photon emission computed tomography (SPECT) apparatus for detecting gamma rays emitted from a radioisotope given to a body to be examined, comprising:

three focus collimators and corresponding detectors arranged at 120° intervals and each capable of rotating 120° around the body for providing detection data;

means for processing said detection data to produce reconstruction data corresponding to a density distribution tomographic image of the radioisotope in said body; and holding mechanisms for positioning a compensation radioisotope at the focus point of each focus collimator on a structure which rotates together with each focus collimator and corresponding detector upon rotation of each focus collimator and corresponding detector around the body.

6. The SPECT apparatus according to claim 5, further comprising:

means for selectively exposing and shielding said compensation radioisotope at each said holding mechanism to permit exposition and shielding of said compensation radioisotope on the side of said focus collimator and said detector.

7. The SPECT apparatus according to claim 5, wherein said structure is a container for said focus collimator and said detector.

8. The SPECT apparatus according to claim 6, wherein said structure is a container for said focus collimator and said detector.

* * * * *